(12) United States Patent
Despalle de Béarn

(10) Patent No.: US 10,575,938 B2
(45) Date of Patent: Mar. 3, 2020

(54) LUMINAL ENDOPROSTHESIS

(71) Applicant: Olivier Despalle de Béarn, Brussels (BE)

(72) Inventor: Olivier Despalle de Béarn, Brussels (BE)

(*) Notice: Subject to any disclaimer, the term of this patent is extended or adjusted under 35 U.S.C. 154(b) by 50 days.

(21) Appl. No.: 15/548,939

(22) PCT Filed: Feb. 4, 2015

(86) PCT No.: PCT/EP2015/052305
§ 371 (c)(1),
(2) Date: Aug. 4, 2017

(87) PCT Pub. No.: WO2016/124235
PCT Pub. Date: Aug. 11, 2016

(65) Prior Publication Data
US 2018/0036111 A1    Feb. 8, 2018

(51) Int. Cl.
| | | |
|---|---|---|
| *A61F 2/07* | (2013.01) | |
| *A61F 2/90* | (2013.01) | |
| *A61F 2/06* | (2013.01) | |
| *A61F 2/24* | (2006.01) | |
| *A61F 2/852* | (2013.01) | |

(52) U.S. Cl.
CPC ............ *A61F 2/07* (2013.01); *A61F 2/06* (2013.01); *A61F 2/2418* (2013.01); *A61F 2/852* (2013.01); *A61F 2/90* (2013.01); *A61F 2002/065* (2013.01); *A61F 2002/067* (2013.01); *A61F 2230/001* (2013.01); *A61F 2240/001* (2013.01); *A61F 2250/0039* (2013.01)

(58) Field of Classification Search
None
See application file for complete search history.

(56) References Cited

U.S. PATENT DOCUMENTS

| | | | | |
|---|---|---|---|---|
| 5,254,662 A | * | 10/1993 | Szycher | A61L 27/18 528/67 |
| 5,741,324 A | | 4/1998 | Glastra | |
| 2010/0016940 A1 | * | 1/2010 | Shokoohi | A61F 2/856 623/1.11 |
| 2013/0073026 A1 | | 3/2013 | Russo et al. | |

FOREIGN PATENT DOCUMENTS

| | | |
|---|---|---|
| WO | 199740779 A1 | 11/1997 |
| WO | 20110143263 A2 | 11/2011 |
| WO | 2014159746 A1 | 10/2014 |

* cited by examiner

*Primary Examiner* — Leslie Lopez
(74) *Attorney, Agent, or Firm* — Burns & Levinson, LLP; Bruce D. Jobse

(57) ABSTRACT

Flow-regulating luminal endoprosthesis (30) comprising a first sections and a second section characterised in that at an end (35) of the endoprosthesis, the second section is turned over on the inside or the outside of the first section in such a way as to form an endoprosthesis (30) comprising two substantially coaxial sections (31, 32) and a turnover part (33) that joins the two sections (31, 32), with the turnover part (33) being located at an end (35) of the endoprosthesis (30) and method pour manufacturing the endoprosthesis (30).

4 Claims, 9 Drawing Sheets

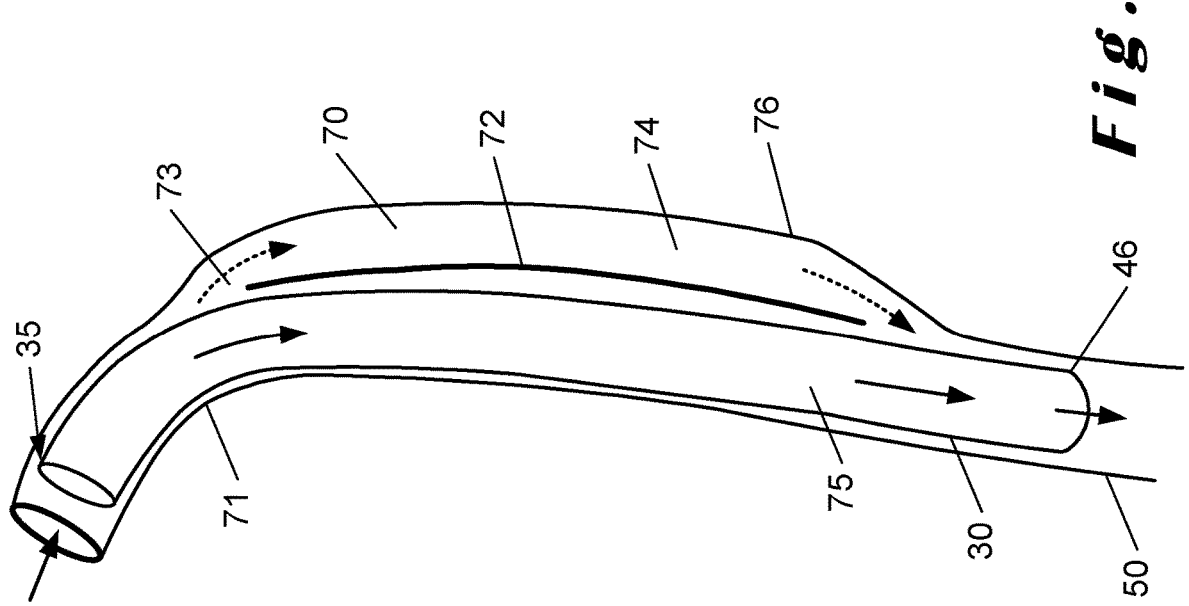
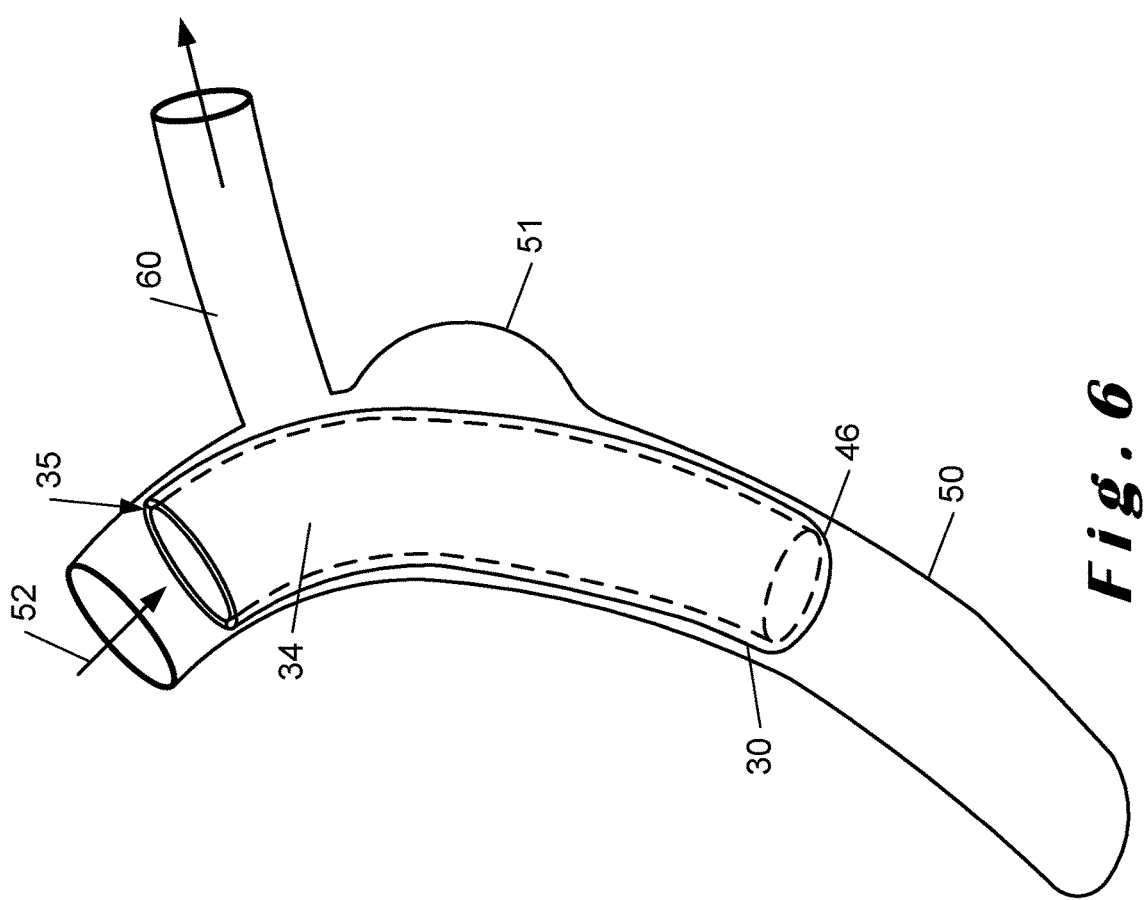

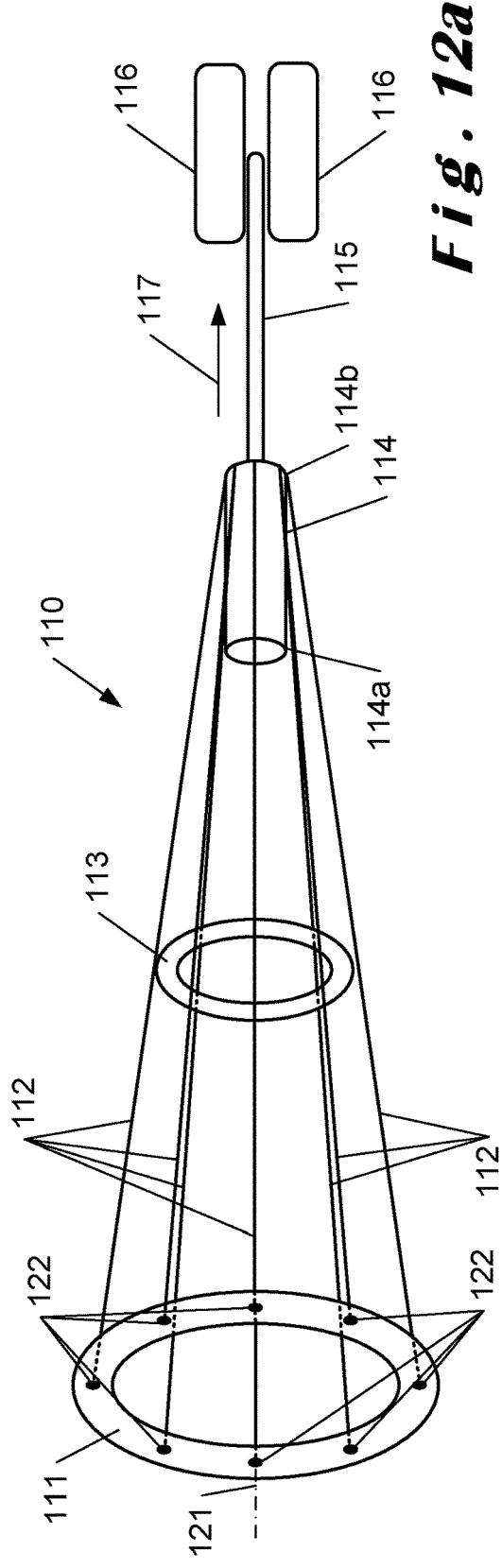
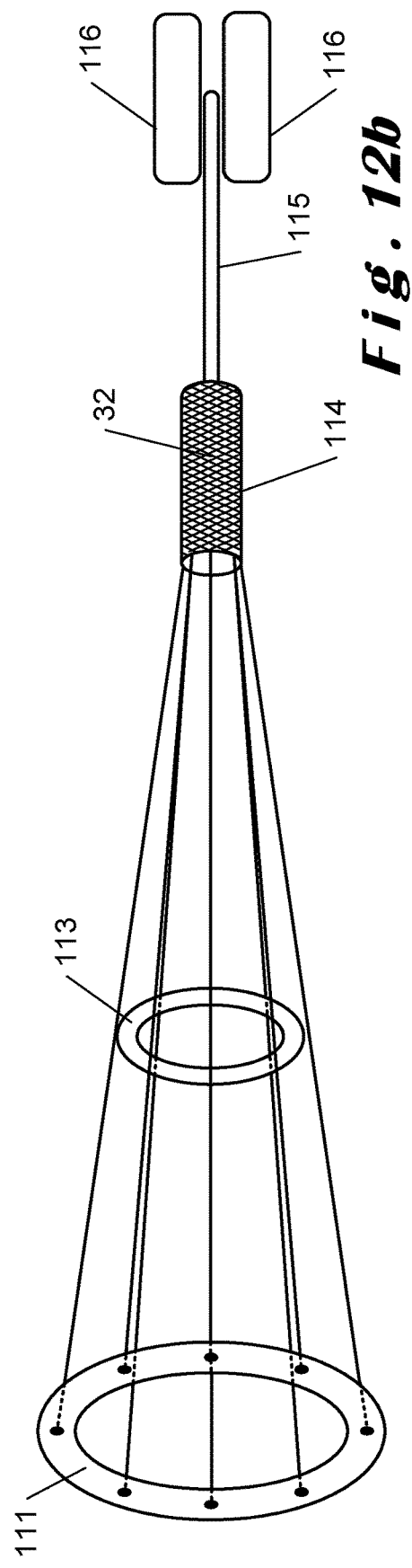
Fig. 12a
Fig. 12b

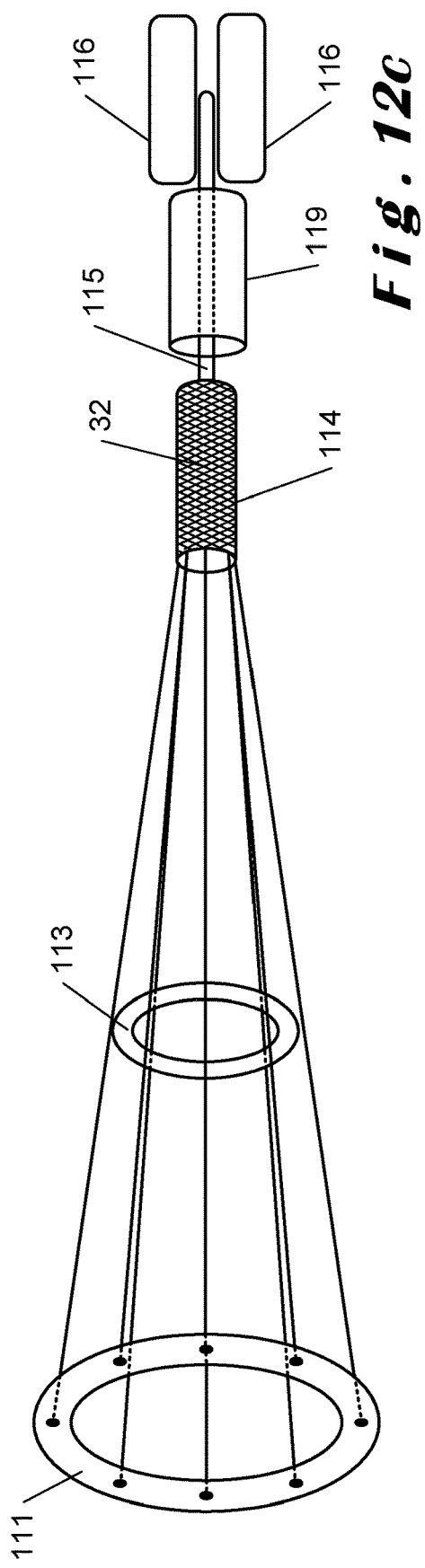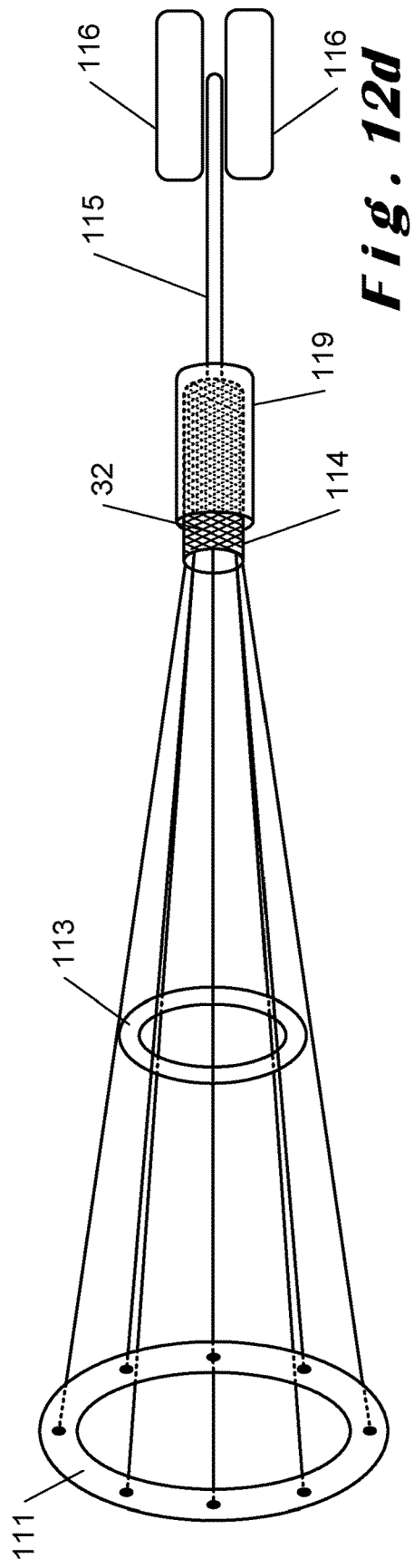

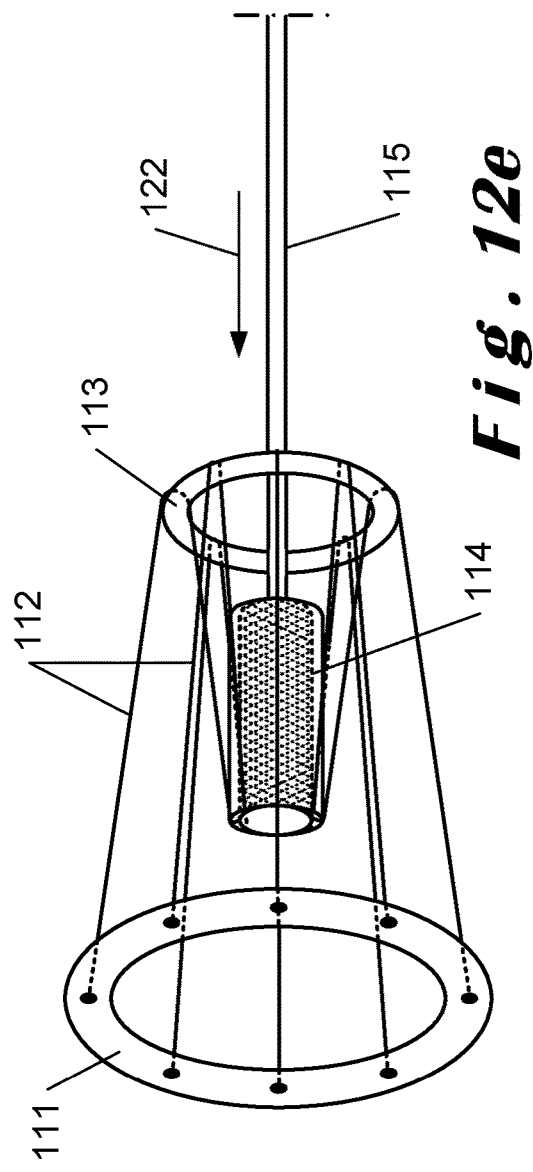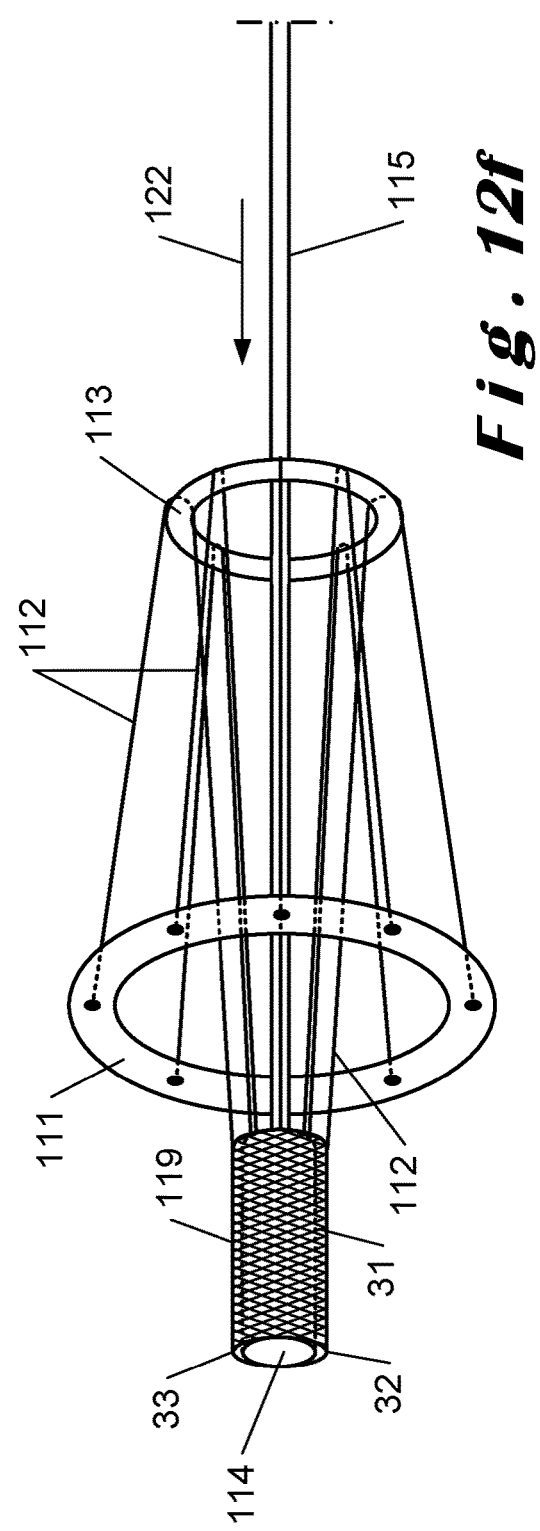

LUMINAL ENDOPROSTHESIS

CROSS-REFERENCE TO RELATED APPLICATIONS

This application is a U.S. national stage application under 35 U.S.C. 371 of co-pending International Application No. PCT/EP20151052305, filed on Feb. 4, 2015, and entitled LUMINAL ENDOPROSTHESIS, which is incorporated by reference herein in its entirety for all purposes.

TECHNICAL FIELD

This invention relates to a flow-regulating luminal endoprosthesis comprising a first substantially cylindrical section and a second substantially cylindrical section.

PRIOR ART

A luminal endoprosthesis is a medical device intended to be implanted inside the hole of an organ (i.e. in the lumen of an organ).

A luminal endoprosthesis is disclosed in document EP1769774A1. This endoprosthesis comprises a cylindrical frame made of interlaced metal wires using a braiding technique described in document EP1942832B1.

Unfortunately, such an endoprosthesis has for disadvantage that the ends of the metal wires that form it are free at the two ends of the endoprosthesis. These free ends of metal wires form elements that scratch the wall of the organ wherein the endoprosthesis is inserted, which results in lesions of this wall, in particular at the proximal end of the endoprosthesis. This phenomenon is particularly marked when the endoprosthesis is used in an artery due to movements of the artery under the effect of the pulses caused by the blood flow and due to the beating of the heart. These lesions can lead to perforations, lacerations, dissections or ruptures of the wall of the organ wherein the endoprosthesis is inserted, which results in serious medical problems.

DISCLOSURE OF THE INVENTION

The invention propose to this effect a flow-regulating luminal endoprosthesis comprising at least one first section and one second section characterised in that at an end of the endoprosthesis, one of the sections is turned over with respect to the other section in such a way as to form an endoprosthesis comprising two substantially coaxial sections and a turnover part that joins the two sections and located at an end of the endoprosthesis.

The turning over of a section with respect to the other at an end of the endoprosthesis makes it possible that this end does not comprise any element that has a free end that risks causing lesions of the wall of the organ wherein the endoprosthesis is inserted. Indeed, when a section is turned over with respect to the other, with the elements of the sections having sharp edges, for example metal wires, are extended from one section to the other and do not comprise, at this end of the endoprosthesis, a free end that risks scratching the wall of the organ wherein the endoprosthesis is inserted.

The endoprosthesis according to the invention can include one or several of the following characteristics, taken separately or in combination with one another:
the first section is turned over on the inside of the second section,
the first section is turned over on the outside of the second section,
the first and second sections and the turnover part comprise a meshing,
the meshing is braided,
the meshing gives rise to rhombic meshes,
the rhombic meshes have at least one angle between 130° and 160°,
the rhombic meshes have a small diagonal which is substantially parallel to an axis of the sections,
the endoprosthesis comprises at least one metal wire,
the metal wire comprises a cobalt/chromium/nickel alloy or a nickel/titanium alloy,
the sections comprise a material of which the elastic modulus is between 0.050 $N/m^2$ and 1 $N/m^2$,
the sections are separated by 0.5 mm to 4 mm,
the endoprosthesis further comprises a means for increasing the radial crushing resistance arranged between the first and the second sections,
the endoprosthesis further comprises at least one valve fastened to the turnover part, and
the sections are substantially cylindrical and have substantially circular sections.

This invention also relates to a method for manufacturing a flow-regulating luminal endoprosthesis comprising a first and a second substantially coaxial sections and a turnover part that joins the two sections, with the method comprising the following steps:
manufacturing of the first section,
manufacturing of the turnover part, and
manufacturing of the second section.

The method according to the invention can include one or several of the following characteristics, taken separately or in combination with one another:
a passing of the first section which is an inside section, in the hole of a ring,
the manufacture of the first section, the manufacture of the turnover part and the manufacture of the second section entail a braiding,
the braiding of the first section, the braiding of the turnover part and the braiding of the second section are carried out with the same wires,
the wires comprise a metal material,
the braiding of the first section is carried out by wires that pass outside the ring and the braiding of the second section is carried out by wires that pass outside and inside the ring,
a tube surrounds the first inside section during the manufacture of the second section,
a moulding of the endoprosthesis in order to create a multi-channel endoprosthesis by joining opposite segments to one another along the wall of the endoprosthesis,
a seam of the segments joined, and
an inserting of at least one endoprosthesis in the multi-channel endoprosthesis.

BRIEF DESCRIPTION OF THE FIGURES

Other characteristics and advantages of the invention shall appear when reading the following detailed description for the comprehension of which reference will be made to the annexed figures among which.

FIG. 6 shows an alternative of the endoprosthesis according to the invention in an artery with an aneurysm;

FIG. 7 shows the endoprosthesis according to the invention in an artery with a dissection;

FIGS. 12a, 12b, 12c, 12d, 12e and 12f show the steps of a method for manufacturing the endoprosthesis according to the invention;

EMBODIMENTS OF THE INVENTION

Figure 1:
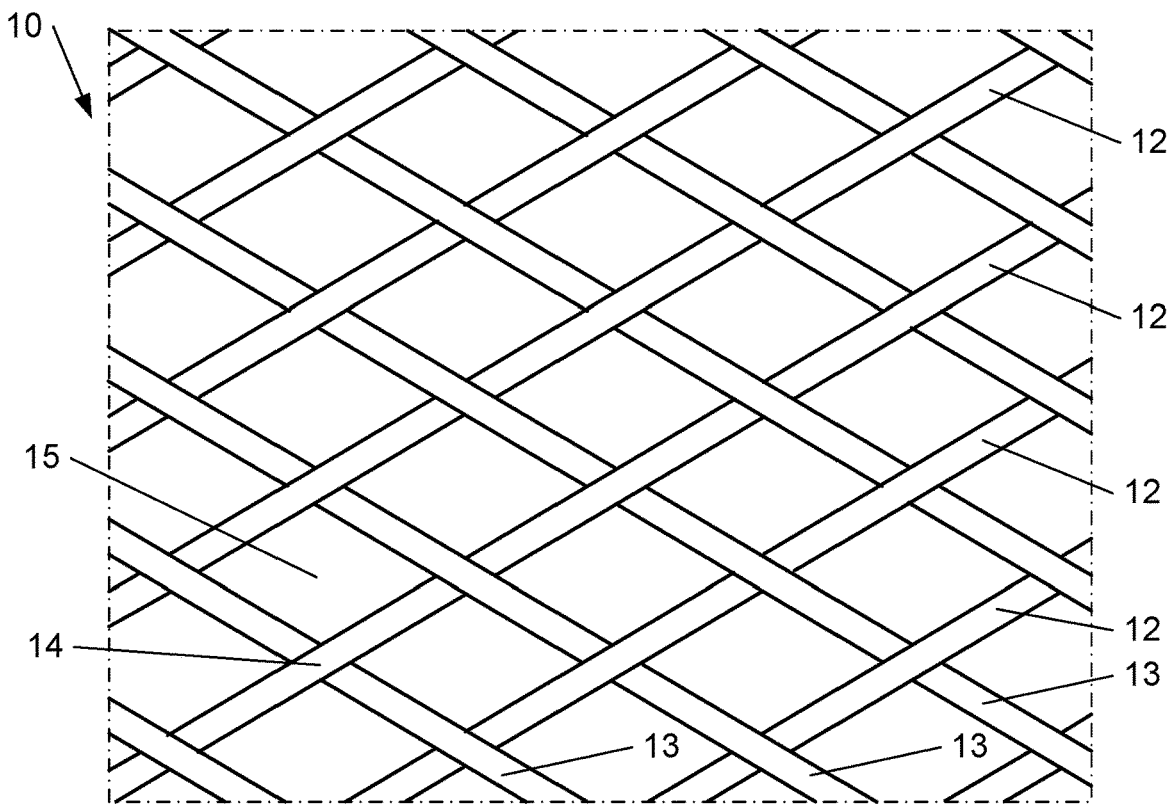
FIG. 1 shows a close-up view of a meshing according to an embodiment of the invention.

This invention is described with particular embodiments and references to figures but the invention is not limited by the latter. The drawings or figures described are only diagrams and are not limiting. In the drawings, certain elements are not to scale.

In the figures, identical or similar elements can bear the same references.

In this document, the adjective "proximal" refers to the portion of an element upstream in relation to a flow. For example, in an artery, a proximal portion of an element is the portion that is closest to the heart as it is the portion upstream in relation to the blood flow.

In this document, the adjective "distal" refers to the portion of an element downstream in relation to a flow. For example, in an artery, a distal portion of an element is the portion the farthest away from the heart as it is the portion downstream in relation to the blood flow.

FIG. 1 shows a close-up view of a meshing 10 according to an embodiment of the invention. Substantially parallel wires 12 having a direction going from the bottom-left to the top-right are intertwined with substantially parallel wires 13 having a direction going from the top-left to the bottom right as shown in FIG. 1, but other ways of braiding the wire are possible without leaving the scope of the invention. A wire 12 alternately passes over and under wires 13 and a wire 13 alternately passes over and under wires 12. The meshing 10, sometimes called weft, carried out by the wires 12, 13 is such that a mesh 15 formed of two pieces of wires 12 and of two pieces of wires 13 substantially has a diamond shape, in other words, the mesh 15 is preferably rhombic. Other shapes are possible for the mesh 15, for example, a square shape (which is a particular type of diamond), the shape of a rectangle, of a parallelogram, of a triangle, of a pentagon, hexagon, or any polygon.

In an embodiment of the invention, at the locations where a wire 12 passes over or under a wire 13, i.e. at the crossovers 14 of the meshing 10, the wires 12, 13 adhere to one another. In another embodiment of the invention, the wires 12, 13 do not adhere one to the other at the crossovers 14.

The wires 12, 13 are preferably made from a biocompatible and non-ferromagnetic material. The wires 12, 13 preferably comprise a metal material. The wires 12, 13 are preferably made of a cobalt/chromium/nickel alloy (Co/Cr/Ni) such as phynox (brand of the Aperam Alloys Imphy company), with the phynox also being referred to as Elgiloy (brand of Elgiloy Specialty Metals, American Gage & Machine Company, American Gage & Machine Company Corporation ILLINOIS and COMBINED METALS OF CHICAGO), or made of a memory metal such as a nickel/titanium (Ni/Ti) alloy such as nitinol. The wires 12, 13 can also be made from a bio-compatible polymer, comprise metal wires covered with a bio-compatible material or comprise a bio-compatible polymer.

In a preferred embodiment of the invention the wires 12, 13 are made from the same material, but they can be made from different materials without leaving the scope of the invention. For example, two out of three wires can be made of phynox and one wire out of three can be made of nitinol in order to improve the shape memory in relation to an endoprosthesis entirely made of phynox. Another example is an endoprosthesis wherein one wire out of five is made of gold in order to improve the radio-opacity of the endoprosthesis, which makes it possible that it is easily detected at radiography.

The wires 12, 13 are preferably made from a slightly elastic material. The elastic modulus of the material of the wires 12, 13 is preferably between 0.050 N/m$^2$ and 1/m$^2$ (between 50 kN/mm$^2$ and 1000 kN/mm$^2$), more preferably between 0.100 N/m$^2$ and 0.500 N/m$^2$, even more preferably in the neighbourhood of 0.200 N/m$^2$ (i.e. 200 kN/mm$^2$).

The wires 12, 13 preferably have a diameter between 0.01 μm and 350 μm. The wires 12, 13 more preferably have a diameter between 10 μm and 220 μm. The wires 12, 13 even more preferably have a diameter of 120 μm, 150 μm or 180 μm.

The meshing 10 is preferably such that its surface has a porosity of 60 to 75%. The meshing 10 is more preferably such that its surface has a porosity close to 70%. The porosity can be modified via a modification in the number of wires or through a modification of the angles of the rhombic meshes 15.

Figure 2:
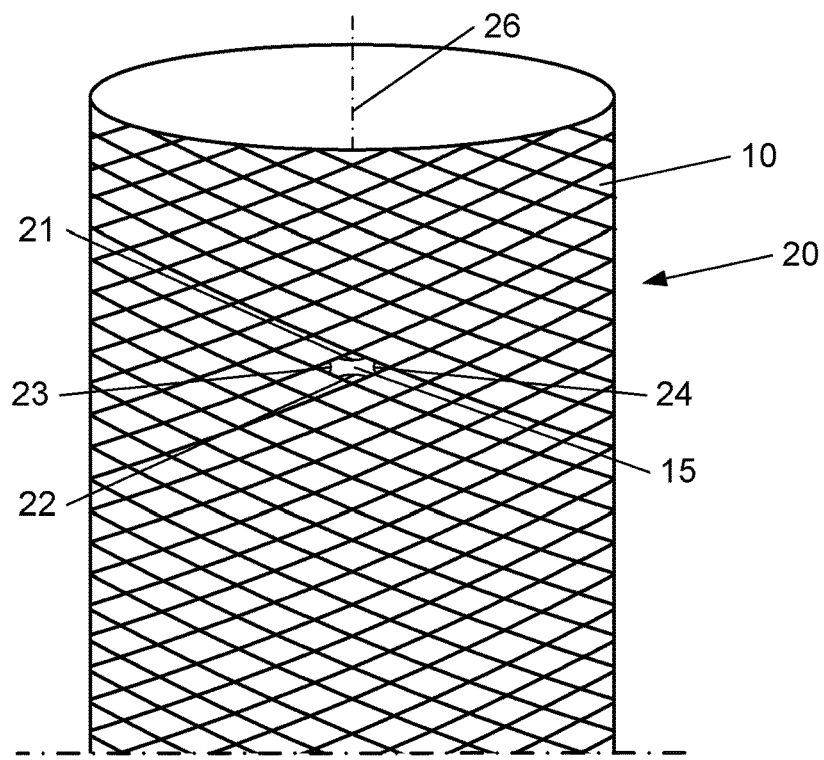
FIG. 2 shows a section according to an embodiment of the invention.

FIG. 2 shows a section 20 according to an embodiment of the invention. The section 20 is hollow, substantially of a cylindrical shape with a circular section and has an axis of revolution 26. The section 20 is preferably a braided assembly of wires 12, 13 that intertwine as a simple weft according to the meshing 10 shown in FIG. 1.

The meshing 10 is preferably such that the large diagonal of the diamond which is the mesh 15 is substantially perpendicular to the axis 26 of the section 20 and the small diagonal of the diamond which is the mesh 15 is substantially parallel to the axis 26 of the section 20, but other inclinations of the meshing 10 or of another meshing are possible without leaving the scope of the invention. The angles 21 and 22 of which the bisector is the small diagonal of the diamond are equal and preferably between 130° and 160° and more preferably in the neighbourhood of 145°, and the angles 23 and 24 of which the bisector is the large diagonal of the diamond are equal and preferably between 30° and 50° and more preferably around 35°, in such a way that the consecutive angles of the diamond are complementary. The meshes 15 preferably have sides between 1 mm and 2 mm.

The section 20 preferably has a diameter between 1 mm and 50 mm. The meshes preferably have sides of a length such that a turn of the section 20 is carried out with between 30 and 200 lines of meshes, with a line of meshes being a set of meshes that follow one another and for which the large or the small diagonals follow each other.

Figure 3:
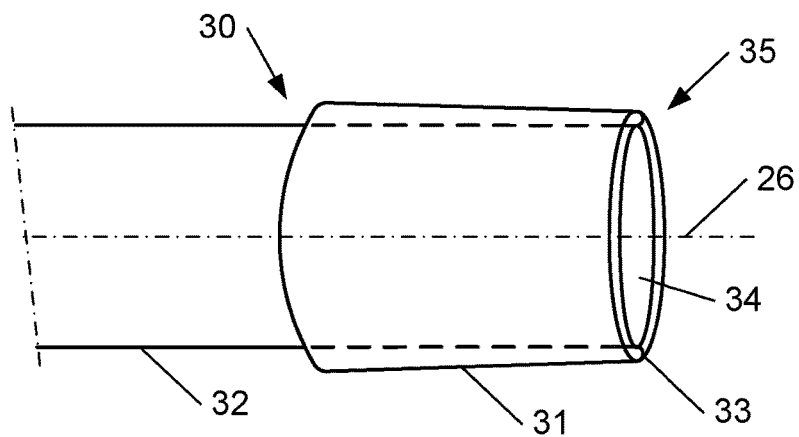
FIG. 3 shows a portion of an endoprosthesis according to the invention comprising a proximal end of the endoprosthesis according to the invention.

FIG. 3 shows a portion of an endoprosthesis 30 according to the invention comprising a proximal end 35 of the endoprosthesis 30. The endoprosthesis comprises an outside section 31, an inside section 32 and a turnover part 33. The portion of space inside the inside section 32 is the lumen 34 of the endoprosthesis 30.

Each one of the inside 32 and outside 31 sections is a section 20 such as shown in FIG. 2. The sections 31, 32 are substantially cylindrical and coaxial when the endoprosthesis 30 is not inserted into an organ and when the endoprosthesis 30 is inserted into an organ, their shape adapts to the organ. The axis 26 already shown in FIG. 2 is an axis for the sections 31, 32 and for the endoprosthesis 30.

In the endoprosthesis 30, the superposition of the two sections 31, 32 makes it that the meshing seen from the outside of the endoprosthesis 30 has a pitch on the average that is smaller than the pitch of the meshing 10 of one of the sections 31, 32 taken separately as shown in FIG. 1. Consequently, in the endoprosthesis 30, the superposition of the two sections 31, 32 makes it that the meshing seen from the outside of the endoprosthesis 30 has a mesh that on average is smaller than the mesh of the meshing 10 of one of the sections 31, 32 taken separately as shown in FIG. 1. It is the superposition of the two sections 31, 32 with these surface meshes that on the average are smaller which creates the total porosity of the endoprosthesis 30.

Figure 4:
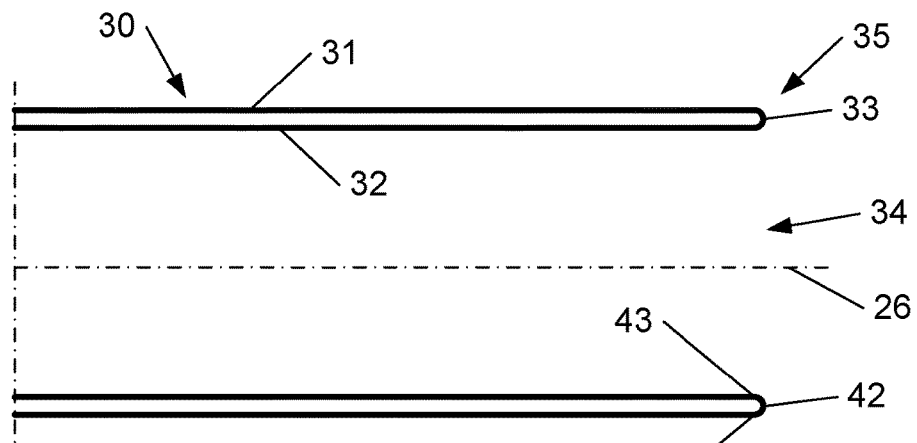
FIG. 4 is a cross-section view of a portion of the endoprosthesis according to the invention comprising the proximal end of the endoprosthesis.

FIG. 4 is a cross-section view of a portion of the endoprosthesis 30 according to the invention comprising the proximal end 35 of the endoprosthesis 30, with the cross-section being in a plane passing through the axis 26. When the endoprosthesis 30 is not in place in an organ, the sections 31, 32 are substantially straight in the direction of the axis 26 and have walls substantially parallel to the axis 26. When the endoprosthesis 30 is in place in an organ, the sections 31, 32 follow the form of the lumen on the organ and their walls are no longer necessarily parallel. It occurs that the sections 31, 32 come closer to one another, in particular in the locations where the organ is curved.

The turnover part 33 acts as a junction between the sections 31, 32. The turnover part 31 comprises a first portion 41 in the extension of the outside section 31 and which bends little by little in order to join a second portion 42 which is substantially in a plane perpendicular to the axis 26 and a third portion 43 in the extension of the inside section 32 and which bends little by little in order to join the second portion 42.

In a preferred embodiment of the invention, the inside 32 and outside 31 sections are lengths that are substantially equal in such a way that the outside section 31 entirely covers the inside section 32. However, in alternative embodiments of the invention, the outside section 31 can be longer or shorter than the inside section 32. For reasons of clarity, the portion shown of the outside section 31 is shorter than the portion of the inside section 32 in FIG. 3.

The sections 31, 32 and the turnover part 33 are preferably made from a weft of continuous wire, in such a way that the continuity of the wires of the sections 31, 32 is not interrupted, in particular in the turnover part 33.

In the endoprosthesis 30, the metal wires continue inside the inside section 32, the turnover part 35 and the outside section 31. Thanks to this, the distal portion 34 of the endoprosthesis 30 does not comprise any free ends, i.e. tips, of metal wires that could damage or tear the wall of the organ wherein the endoprosthesis 30 is inserted, with these free ends being pointed and sharp. The endoprosthesis 30 does not have a point of rupture or welding or cutting weakness of the intersections of the wires.

The diameter of the endoprosthesis 30 is preferably between 1 mm and 50 mm. The diameter of the wires 12, 13 is preferably chosen according to the diameter of the endoprosthesis 30.

The distance 44 between the two sections 31, 32 is determined by the turnover part. The distance 44 is preferably in an interval from 0.5 mm to 4 mm. The distance 44 is preferably about 2 mm.

In a preferred embodiment of the invention, the two sections 31, 32 do not move in relation to one another in a direction parallel to the axis 26, two meshes that face one another during the manufacture of the endoprosthesis will always face each other.

The portion of space delimited by the two sections 31, 32 and the turnover part 33 is an inter-section space 45. The endoprosthesis 30 according to the invention makes it possible to insert an inter-section space structure 45 in the inter-section space 45, for example a structure made of metal or nitinol in order to increase the radial force of the endoprosthesis 30.

According to an embodiment of the invention, at a distal end 46 of the endoprosthesis 30, the ends of the sections 31, 32 are not very aggressive for the wall of the organ wherein the endoprosthesis is inserted. For example, the wires 12, 13 of the sections 31, 32 are laser cut, which forms small balls at the end of the wires due to the heat of the laser. The wires 12, 13 of the sections 31, 32 can be cut by mechanical means such as scissors and be treated par electro-polishing in order to round off each wire end.

Thanks to the braided structure of the wires 12, 13, the endoprosthesis 30 according to the invention has sufficient flexibility to follow the shape of the ducts of the organs, in particular blood vessels.

The radial force, i.e. the radial crushing resistance, of the endoprosthesis 30 according to the invention is the result of the following compromise.

On the one hand, the radial force of the endoprosthesis 30 is large enough to prevent the endoprosthesis 30 from closing. In particular, the radial force of the endoprosthesis 30 is greater on its proximal end 35 than on the rest of its structure thanks to the second portion 42 of the turnover part 33 which has a high component in a plane perpendicular to the axis 26, otherwise a radial component.

On the other hand, the radial force of the endoprosthesis 30 is small enough to allow the diameter of the endoprosthesis 30 to become minimum when the endoprosthesis 30 is stretched, in such a way that the endoprosthesis 30 can slide into a catheter in order to be inserted into organs such as blood vessels.

The fact that the radial force of the endoprosthesis 30 is greater in its proximal portion than in its distal portion is particularly interesting in the case of an endoprosthesis intended to be placed in the aorta, because the diameter of the aorta decreases as it moves away from the heart. Indeed, the endoprosthesis 30 placed in the aorta then shrinks its diameter in its distal portion under the pressure of the wall of the aorta, while still retaining a larger diameter in the proximal portion thereof, where the diameter of the aorta is larger.

The endoprosthesis 30 according to the invention has a good reliability and good maintaining of its shape over time because it does not have a point of rupture or welding or cutting weakness of the intersections of the wires and thanks to the excellent biocompatibility of the material chosen (for example phynox)

In a preferred embodiment of the invention, the endoprosthesis 30 does not comprise any textile covering. However, the endoprosthesis 30 according to the invention could comprise one without leaving the scope of the invention.

In an embodiment of the invention, the sections 31, 32 are fastened, by welding for example, to one another in the distal portion of the endoprosthesis, in order to prevent the sections from sliding in relation to one another during the placement of the endoprosthesis 30.

In an embodiment of the invention, certain meshes are fastened on crossovers but not all or certain wires are fastened together on crossovers but not all. For example, the meshes are fastened only on a proximal portion of the endoprosthesis but not on a distal portion, or certain wires are detached two-by-two over a distal portion of the endoprosthesis.

In an embodiment of the invention wherein the meshes are not fastened on crossovers, it is possible to pass through the wall of the endoprosthesis 30 with a guide then a balloon and finally a stent in order to treat a stenosis on a vessel of which the entry opens onto the endoprosthesis 30 because the meshes separate in order allow for the passage then they return to their place.

In an embodiment of the endoprosthesis 30 according to the invention that is specifically provided for the aorta, the endoprosthesis 30 has a diameter of approximately 30 mm, a length of approximately 150 mm, rhombic meshes with a large diagonal of approximately 2 mm and a porosity of about 65%.

Although this invention is primarily described as comprising two coaxial sections 31, 32, an endoprosthesis that comprises more than two sections and at least one turnover part does not leave the scope of the invention. For example, an endoprosthesis that comprises four sections would have the advantage that an end of the endoprosthesis does not comprise any elements ne comprises any element that has a free end that risks causing lesions of the wall of the organ wherein the endoprosthesis is inserted while still being more rigid than the endoprosthesis that comprises only two sections.

Figure 5:
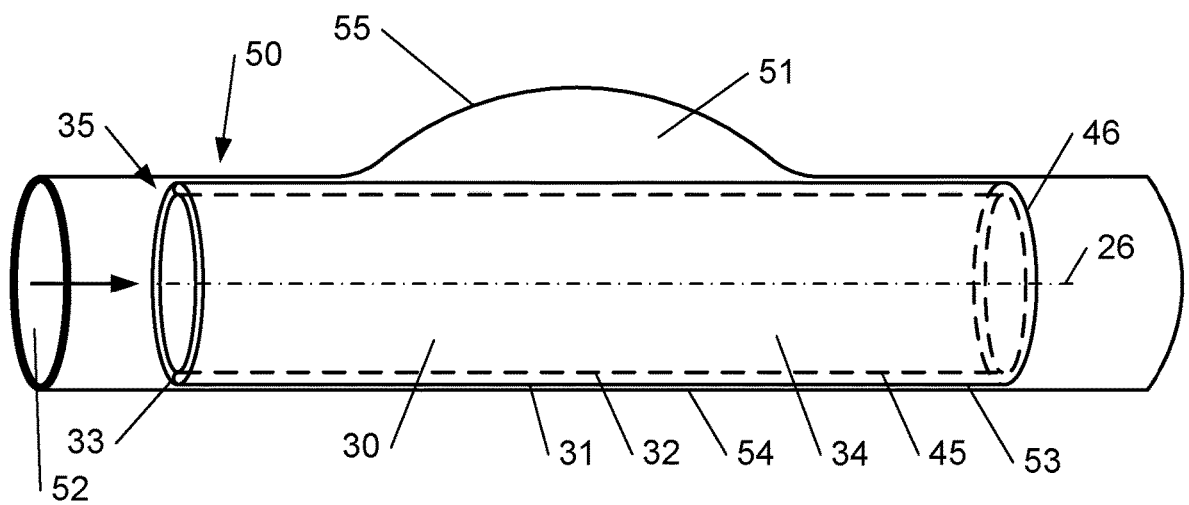
FIG. 5 shows an endoprosthesis according to the invention in an artery with an aneurysm.

FIG. 5 shows an endoprosthesis according to the invention in an artery 50 with an aneurysm 51, which is a localised dilatation of a wall 54 of the artery. The endoprosthesis according to the invention is preferably used in blood vessels, in particular the aorta or in the cranium, for cases of aneurysm or dissection, but it can also be used for cases of atherosclerosis and of stenosis. An endoprosthesis according to the invention can also be used in veins. An endoprosthesis according to the invention can also be used in organs other than blood vessels that have a lumen such as the intestine.

An endoprosthesis such as that of the invention is sometimes called a stent, stent graft or stent for blood vessel. The endoprosthesis according to the invention is qualified as "flow-regulating" through its regulating action on the dynamics of the flow of the liquid passing in the lumen of the organ wherein the endoprosthesis is inserted.

The blood flow is represented by an arrow 52 in FIG. 5. The endoprosthesis 30 is placed in such a way that the turnover part 33 is on the side where the blood comes from, i.e. on the proximal side according to the convention of this document.

The blood passes primarily in the lumen 34 of the endoprosthesis 30 but also in the inter-section space 45 and in a space 53 located between the endoprosthesis 30 and the wall 54 of the artery.

Thanks to the arrangement of the wires 12, 13 of the outside section 31 with respect to the wires 12, 13 of the inside section 32, in other words thanks to the superposition of two offset meshings and separated by a distance 44, the endoprosthesis 30 modifies the dynamics of the blood in such a way that the blood circulating in the space 53 is directed in the direction of the axis 26 and that the blood flow is accelerated in the lumen 34. The endoprosthesis 30 therefore has for effect that the circulation of the blood is better in the artery in the presence of the endoprosthesis 30 than in the absence of the endoprosthesis 30.

The endoprosthesis 30 according to the invention makes it possible to adjust the blood flow by modifying the dynamics of the blood penetrating into the aneurysm 51. Indeed, in the absence of the endoprosthesis 30 according to the invention, the blood flow penetrating into the aneurysm 51 is substantially a turbulent flow that has vortexes. The presence of the endoprosthesis 30 according to the invention allows the blood flow penetrating into the aneurysm 51 to be laminar. This has several positive effects.

On the one hand, the laminar flow instead of being turbulent reduces the blood pressure in the aneurysm and on a wall 55 of the aneurysm 51. This wall 55 is weakened due to the aneurysm and a rupture of the aneurysm can be fatal for the organism. Reducing the pressure that the wall 55 is subjected to therefore reduces the probability of a mortal outcome of the aneurysm 51. Using a covered endoprosthesis does not allow for this effect because it is known that an endoprosthesis covered with a textile transmits about 70% of the pressure way to the wall 55 of the portion of the aneurysm.

On the other hand, a turbulent flow in the aneurysm 51 creates thromboses in the latter, i.e. tissue created by disordered blood clotting that transmits the blood pressure to the wall 55, while a laminar flow creates in the aneurysm 51 thromboses in organised layers that have the effect of damping the pressure. The thromboses in layers as such reduce the pressure exerted by the blood on the wall 55 and consequently reduce the risk of a fatal outcome of the aneurysm 51.

FIG. 6 shows an endoprosthesis 30 according to the invention in an artery 50 with an aneurysm 51. The artery 50 shown in FIG. 6 has a relatively sinuous path to which the shape of the endoprosthesis 30 adapts. The excellent adaptability of the endoprosthesis 30 to the shape of the artery is in particular due to the braiding of the endoprosthesis 30. This braiding in addition gives rise to a low risk of kinking or blocking of the lumen of the endoprosthesis 30 during a twisting of the endoprosthesis 30, because the wires of the endoprosthesis 30 can slide over one another in order to offset the twisting.

The artery 50 shown in FIG. 6 is furthermore provided with a lateral branch 60 in the vicinity of the aneurysm 51. An endoprosthesis of which the walls would prevent the blood from passing into the branch 60 would cause a closing off of the branch 60, with a risk of partial thrombosis or occlusion of this branch. For lumbar or dorsal branches, this generates a risk of full or partial paralysis of the organism. This problem is common for an aneurysm of the aorta close to the renal arteries. The placement of an endoprosthesis of which the walls are hermetic blocks the passage of the blood to one of two of the renal arteries.

On the contrary, the endoprosthesis 30 according to the invention allows the blood present in its lumen 34 to pass into the branch 60 because the sections 31, 32 of the endoprosthesis 30 are not hermetic.

Note that the structure of the endoprosthesis 30 according to the invention, and in particular its radial force, gives rise to good apposition of the ends of the endoprosthesis that makes it possible to prevent type I leaks.

FIG. 7 shows the endoprosthesis 30 according to the invention in an artery 50 with a dissection 70, also called a dissecting aneurysm. The dissection 70 is a detachment of the tunica intima 72 in relation to the other tunics 76 (tunica media and tunica adventitia) of the wall 71 of the artery, with the arterial blood then entering into the space, called a false lumen 74, created by this detachment.

The endoprosthesis 30 is placed in the true lumen 75, which is the hole of the artery 50. The endoprosthesis 30 as such keeps the true lumen 75 open and balances the pressure between the true lumen 75 and the false lumen 74. The endoprosthesis 30 also exerts a radial thrust directed outwards which tends to reduce the diameter of the false lumen 74 by pushing back the tunica intima 72 to the tunica media of the artery and to compress a gateway or gateways 73 of the dissection 70. The thrust exerted by the endoprosthesis 30 is particularly large at the proximal end 35 of the endoprosthesis 30 thanks to the second portion 42 of the turnover part 33 which has a high radial component. As the endoprosthesis 30 is placed in such a way that it covers the gateway with the proximal end 35 of the endoprosthesis 30 close to the gateway 73 of the dissection 70, this particularly large thrust makes it possible to decrease the size of the gateway 73, even close the gateway 73 and as such reduce the quantity of blood that enters into the false lumen 74. This reduction in the quantity of blood that enters into the false lumen 74 makes it possible to reduce the risks, in particular the life-threatening risks, subsequent to the dissection 70.

The fact that the proximal end 35 of the endoprosthesis 30 does not comprise any element having a free end that risks scratching the wall of the organ wherein the endoprosthesis is inserted, thanks to the turning over of a second section inside or outside a first section, is particularly pertinent in the case of a dissection, in particular of the aorta, as a tear on the membrane intima 72 between the true lumen 75 and the false lumen 74 is a mortal risk. As the distal end 46 of the endoprosthesis 30 is not in contact with the membrane intima 72 between the true lumen 75 and the false lumen 74, the risk is not as substantial due to the fact that the distal end 46 of the endoprosthesis 30 can damage the wall of the organ wherein the endoprosthesis 30 is inserted.

Figure 9:
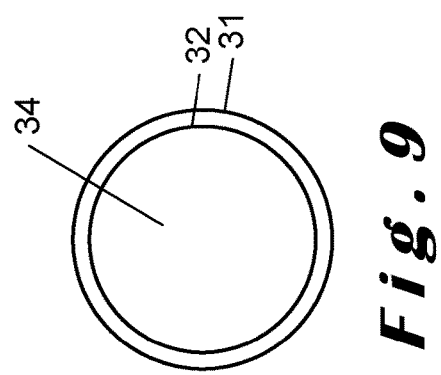
FIG. 9 shows a cross-section according to a plane perpendicular to the axis of the multi-channel endoprosthesis according to the invention.
Figure 10:
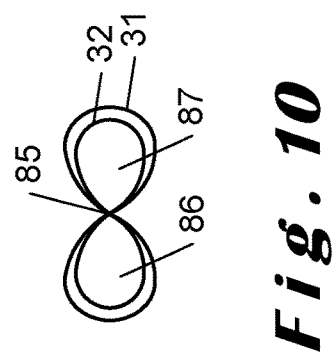
FIG. 10 shows a cross-section according to another plane perpendicular to the axis of the multi-channel endoprosthesis according to the invention.
Figure 8:
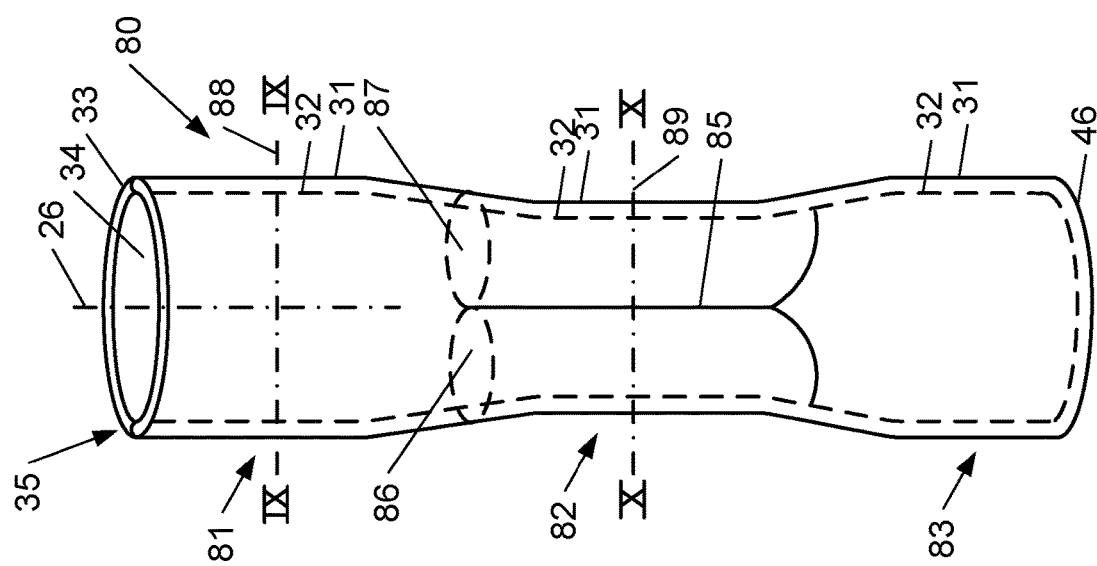
FIG. 8 shows a multi-channel endoprosthesis 80 according to an embodiment of the invention.

FIG. 8 shows a multi-channel endoprosthesis 80 according to an embodiment of the invention. FIG. 9 shows a cross-section according to a plane 88 perpendicular to the axis 26 of the multi-channel endoprosthesis 80, with this plane bearing a reference IX in FIG. 8. FIG. 10 shows a cross-section according to a plane 89 perpendicular to the axis 26 of the multi-channel endoprosthesis 80, with this plane bearing a reference X in FIG. 8. The multi-channel endoprosthesis 80 comprises three parties: a first portion 81 that has a section with a substantially circular shape (FIG. 9), a second portion 82 that has a section substantially in the shape of an 8 (FIG. 10) and a third portion 83 that has a section with a substantially circular shape (FIG. 9).

The first portion 81 is similar to a portion of an endoprosthesis 30 (FIG. 3) according to the invention comprising the proximal end 35 of the endoprosthesis 30. The first portion 81 comprises a portion of the inside section 32, a portion of the outside section 31 and the turnover part 33 of the multi-channel endoprosthesis 80. The third portion 83 is similar to a portion of an endoprosthesis 30 (FIG. 3) according to the invention comprising the distal end 46 of the endoprosthesis 30. The third portion 83 comprises a portion of the inside section 32 and a portion of the outside section 31.

The second portion 82 is similar to a median portion of an endoprosthesis 30 (FIG. 3) according to the invention that does not comprise the proximal end 35 of the endoprosthesis 30, or the distal end 46 of the endoprosthesis 30 and wherein segments parallel to the axis 26 and opposite one another along the wall of the endoprosthesis 30 would have been joined along a seam 85. The second portion 82 has two lumens 86, 87. The second portion 82 comprises a portion of the inside section 32 and a portion of the outside section 31, with the inside 32 and outside 31 sections joining together along the seam 85.

In an alternative embodiment of the multi-channel endoprosthesis 80 the third portion 83 is not present.

Figure 11:
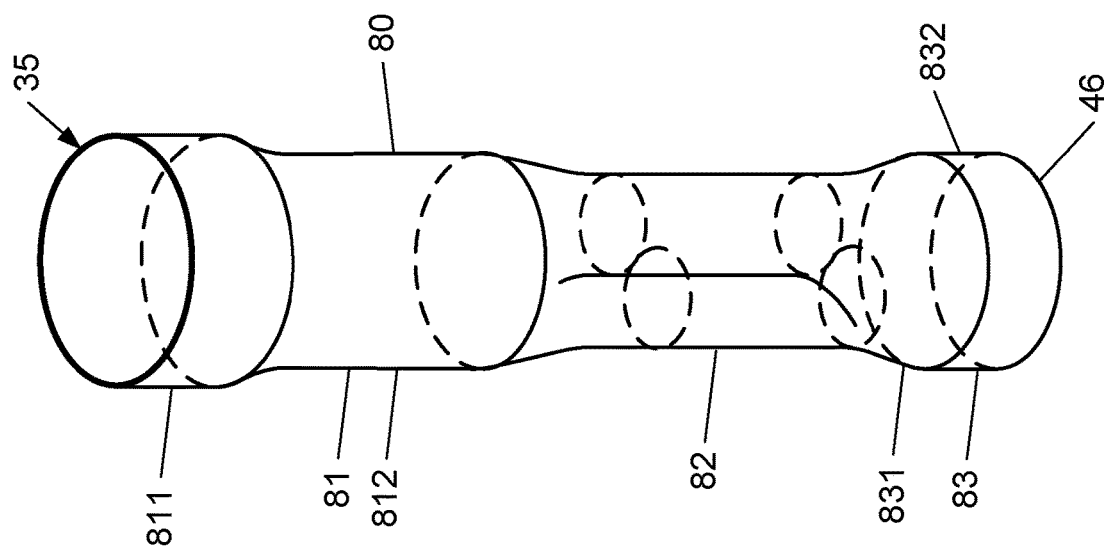
FIG. 11 shows an alternative of the multi-channel endoprosthesis 80 according to the invention.

FIG. 11 shows an alternative of the multi-channel endoprosthesis 80. In this alternative, the first portion 81 of the multi-channel endoprosthesis itself has first portion 811 and a second portion 812. The first portion 811 has a larger diameter than the second portion 812. In this alternative, the third portion 83 of the multi-channel endoprosthesis itself has a first portion 831 and a second portion 832. The first portion 811 has a diameter that is smaller than the second portion 812.

FIG. 12 shows a method for manufacturing the endoprosthesis 30 according to the invention. The elements shown in FIG. 12 are the following:
a ring 111,
wires 112,
a ring 113,
a mandrel 114,
a proximal end 114a of the mandrel 114,
a distal end 114b of the mandrel 114,
a guide 115,
tracks 116,
a first direction 117,
a tube 119,
an axis 121, and
a second direction 122.

For reasons of clarity, the elements of FIG. 12 are not shown to scale and their respective distance is also not to scale.

The ring 111 is arranged to rotate about the axis 121. The ring 111 can comprise a plurality of coaxial rings provided to rotate in the same direction or in opposite directions. The ring 111 comprises weaving shuttles 122 whereon the wires 112 are placed at the beginning of the method. There are generally 148 weaving shuttles 122. The number of weaving shuttles 122 can vary, in particular according to the diameter chosen for the endoprosthesis. In order to avoid complicating FIG. 12, the latter shows only the departure of the wires 112 by points.

The wires 112 are the wires 12, 13 that form the meshing 10 of the sections 31, 32 of the endoprosthesis 30. There are preferably between 50 and 100 wires 112. There are, more preferably, 78 or 80 wires. For reasons of clarity, only some of the wires 112 are shown.

The ring 113 has a diameter that is greater than the outer diameter of the tube 119, in such a way that the tube 119 can pass inside the ring 113.

The mandrel 114 has an outer diameter equal to the diameter of the inside section 32 of the endoprosthesis 30. The proximal end 114a of the mandrel corresponds to the proximal end 35 of the endoprosthesis 30. The distal end 114b of the mandrel corresponds to the distal end 46 of the endoprosthesis 30.

The guide 115 is fastened to the mandrel 114 and comprises means so that the tracks 116 can displace the guide 115 (and consequently the mandrel 114) along the axis 121.

The tracks 116 displace the guide 115 in the two directions along the axis 121. There are preferably two tracks 116.

The first direction 117 is the first direction of movement of the mandrel in relation to the ring 111 and to the ring 113.

The tube 119 is hollow. Its inner diameter is such that the mandrel 114 with the inside section 32 can be inserted inside the tube 119. Its outer diameter is equal to the diameter of the outside section 31. The thickness of the tube 119 is the distance 44 between the inside section 32 and the outside section 31. The tube 119 is preferably of the same length as the mandrel 114.

The axis 121 is the axis of the ring 11, of the ring 113, of the mandrel 114, of the guide 115 and of the tube 119.

The second direction 122 is the second direction of movement of the mandrel in relation to the ring 111 and to the ring 113.

FIG. 12a shows the method according to the invention at the moment of the beginning of the weaving. The wires 112 start from the ring 111, pass around the ring 113, pass around the mandrel 114 and are attached to the distal end 114b of the mandrel. In an embodiment of the invention, the wires 112 will have been laser cut beforehand, which forms small balls at the end of the wires due to the heat of the laser.

The tracks 116 displace the guide 115 and the mandrel 114 in the first direction 117, i.e. towards the right in FIG. 12. At the same time, the rings of the ring 111 rotate in such a way as to form the weaving 10 for the inside section 32 around the mandrel 114.

The ring 113 can also make it possible to retain a braiding angle determined with respect to the axis of the system.

FIG. 12b shows the method according to the invention after the weaving of the inside section 32 on the mandrel 114. The movement of the guide 115 and of the mandrel 114 stops at this moment as well as the movement of the ring 111.

FIGS. 12c and 12d show the following step of the method according to the invention. The tube 119 is inserted around the inside section 32 which is itself around the mandrel 114 in such a way that the end of the tube 119 is at the same height as the proximal end 114a of the mandrel 114. The tube 119 is then blocked with respect to the mandrel 114. The object of the tube 119 is to block the wires 112 at the proximal end 114a of the mandrel in order to form the turnover part 33 of the endoprosthesis 30 and to supply a support for the braiding of the outside section. Another means of blocking the wires 112 at the proximal end 114a of the mandrel could be considered without leaving the scope of the invention. For example, the wires 112 could be blocked by fasteners at the proximal end 114a of the mandrel.

The tracks 116 then displace the guide 115 and the mandrel 114 in the second direction 122, i.e. towards the left in FIG. 12, without causing any rotation of the ring 11. This displacement brings the mandrel 114 and the inside section 32 which covers the mandrel 114 to pass through the hole of the ring 113. This displacement stops when the wires 112 are again under tension.

FIG. 12e shows the method according to the invention at the moment of the beginning of the weaving of the outside section 31. The tracks 116 displace the guide 115 and the mandrel 114 in the second direction 122. At the same time, the rings of the ring 111 rotate in such a way as to form the weaving 10 for the outside section 31 around the tube 119. The wires 112 start from the ring 111, pass from the outside to the inside of the ring 113, pass around the tube 119 and join the proximal end of the first section 32 already braided. The location of the braiding where the wires 112 change direction is the turnover part 33 of the endoprosthesis.

The passage of the mandrel 114 whereon the inside section 32 is braided in the ring 113 allows for the braiding of the turnover part 33 and of the outside section 31 without disconnecting the wires 112. The same wires 112 are therefore used for the inside section 32, the outside section 31 and the turnover part 33. The ring 113 makes it possible for a tension to be present in the wires 112 during the braiding of the outside section 31 and allows the movement of the ring 111 to be reflected in the movement of the wires 112 on the tube 119 for the carrying out of the braiding of the turnover part 33 and of the outside section 31. The ring 113 also makes it possible that the braidings of the inside 32 and outside 31 sections are carried out at the same braiding angle with respect to the axis 121.

FIG. 12f shows the method according to the invention after the weaving of the outside section 31. The meshing of the inside section 32 is not shown in FIG. 12f in order to avoid complicating the diagram. The movement of the guide 115 and of the mandrel 114 stops at this moment as well as the movement of the ring 111.

The wires 112 are then cut at the distal end of the outside section 31, in such a way as to form the endoprosthesis 30. They can be laser cut or in another way.

The tube 119 is removed. The mandrel 114 is removed.

In what follows, the endoprosthesis 30 can undergo additional treatment steps. For example an electro-polishing of the wires 112 in order to round off each wire end, a thermal treatment which consolidates the shape of the endoprosthesis 30 and which glues the meshings of the inside 32 and outside 31 sections or any other step. Another example is a step of stripping the endoprosthesis 30.

In an embodiment of the invention, the endoprosthesis 30 is formed by the braiding of a single section which is then turned over in such a way as to form an inside section 32, an outside section 31 and a turnover part 33. This turning over, or doubling-over, can be carried out using mechanical means or manually.

After the manufacture of the endoprosthesis 30, other elements can be attached to the endoprosthesis, which can be done before the placement of the endoprosthesis 30 in an organism or after the placement of the endoprosthesis 30 in an organism. For example, a valve of the TAVI (Transcatheter Aortic Valve Implantation) type can be attached to the proximal end 35 of the endoprosthesis 30, for example by attaching it to the turnover part 33. The valve and the endoprosthesis 30 are placed at the same time in the organism, at the junction of the heart and of the aorta for the valve and in the aorta for the endoprosthesis 30. The endoprosthesis according to the invention makes possible on the one hand a good fastening of the valve because the turnover part 33 is solidly fastened to the two sections 31, 32 since it is made of the same wires 12, 13 as the sections 31, 32 and on the other hand, the proximal portion of the endoprosthesis according to the invention does not risk damaging the valve since the proximal portion of the endoprosthesis does not comprise any free end of a wire that is aggressive for the valve.

Figure 13:
FIG. 13 shows a hook for fastening an element to the endoprosthesis according to the invention.

The valve TAVI, or another element, can be fastened to the endoprosthesis 30 thanks to hooks such as the one shown in FIG. 13. The hooks are preferably made of the same material as the endoprosthesis 30.

Figure 14:
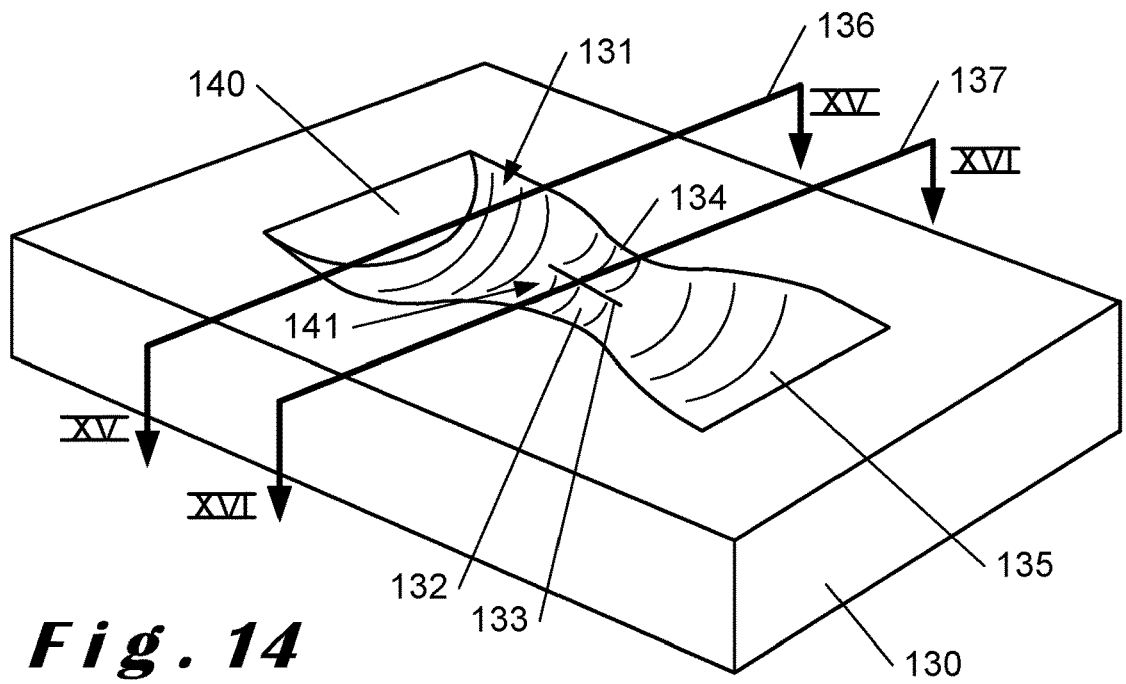
FIG. 14 diagrammatically shows a lower part of a mould used to manufacture a multi-channel endoprosthesis according to the invention.
Figure 15:
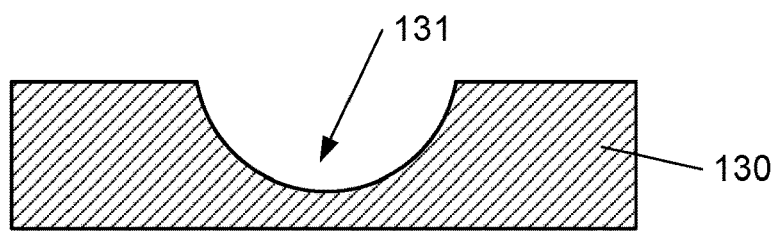
FIG. 15 diagrammatically shows a cross-section of the lower part of the mould used to manufacture a multi-channel endoprosthesis according to the invention.
Figure 16:
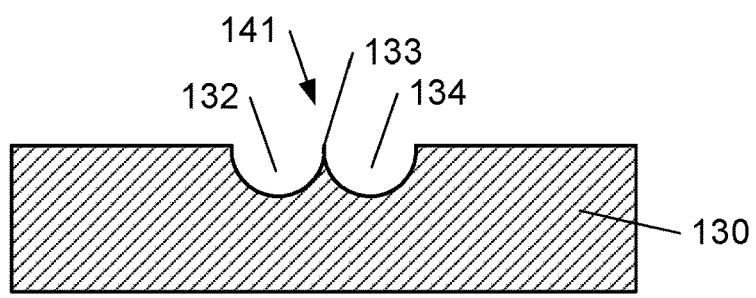
FIG. 16 diagrammatically shows another cross-section of the lower part of the mould used to manufacture a multi-channel endoprosthesis according to the invention.

The multi-channel endoprosthesis 80 according to an embodiment of the invention can be manufactured with a mould of which a lower part 130 is diagrammed in FIG. 14. An upper part of the mould is not shown in the figure because it is substantially identical to the lower part 130. The lower part 130 comprises a hollow 140. FIG. 15 shows a cross-section according to a plane 136, with this plane bearing a reference XV in FIG. 14. FIG. 16 shows a cross-section according to a plane 137, with this plane bearing a reference XVI in FIG. 14. The hollow 140 comprises three parties: a first portion 131 that has a section in the shape of a half-circle (FIG. 15), a second portion 141 that has a section substantially in the shape of a ω (FIG. 16) and a third portion 135 that has a section in the shape of a half-circle (FIG. 15). The second portion 141 itself comprises two portions 132, 134 with a section in the form of a half-circle, separated by an edge 133.

A method for carrying out the multi-channel endoprosthesis 80, using an endoprosthesis 30, is as follows.

An endoprosthesis 30 that has a length less than or equal to the length of the hollow 140, and a diameter less than or equal to the width of the hollow 140 is inserted into the hollow 140. The upper part of the mould is placed on the lower part 130 in such a way that the two parts are facing each other and in such a way that substantially diametrically opposite segments of the endoprosthesis 30 and parallel to the axis 26 join together on the edge 133 in order to form the seam 85 (FIG. 10). A thermal treatment is then preferably applied in order to consolidate the form of the multi-channel endoprosthesis 80. Then, the upper part of the mould is removed and a wire preferably made of the same material as the wires of the endoprosthesis 30 is sewn onto the seam 85 for fastening together the substantially diametrically opposite segments of the endoprosthesis 30, during a step of sewing.

Figure 17:
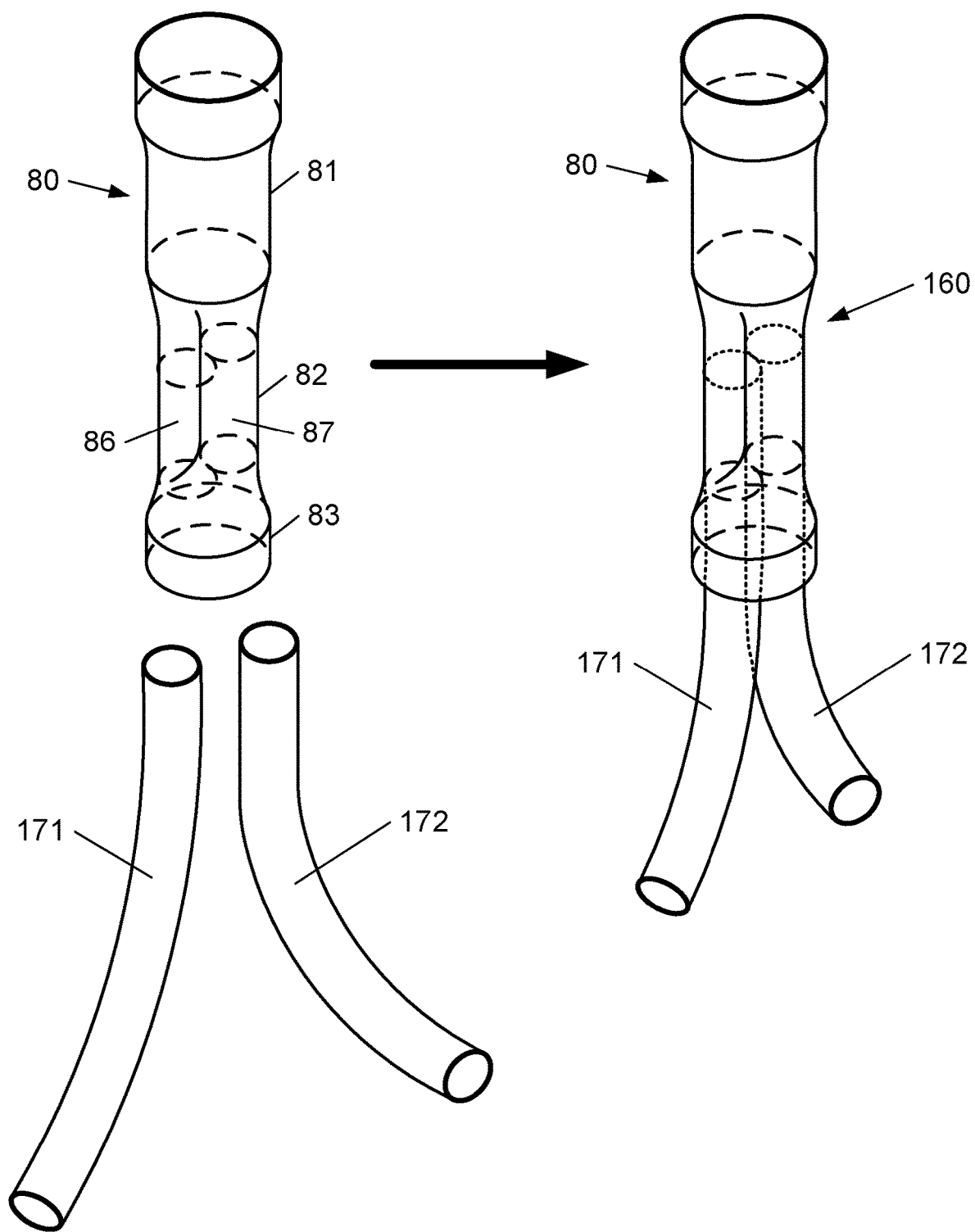
FIG. 17 shows a Y-shaped endoprosthesis according to an embodiment of this invention and a method according to this invention for manufacturing the Y-shaped endoprosthesis.

FIG. 17 shows a Y-shaped endoprosthesis 160 according to an embodiment of this invention and a method for manufacturing the Y-shaped endoprosthesis 160. A first endoprosthesis 171 and a second endoprosthesis 172, of the type of the endoprosthesis 30 shown in FIGS. 3 and 4, are inserted firstly in a third portion 83, then in a second portion 82 of a multi-channel endoprosthesis 80, in such a way that the first endoprosthesis 171 is in a first lumen 86 of the second portion 82 and the second endoprosthesis 172 is in a second lumen 87 of the second portion 82. The diameter of the lumen 86 of the second portion 82 of the multi-channel endoprosthesis 80 is greater than the outer diameter of the first endoprosthesis 171 and the inner diameter of the second lumen 87 of the second portion 82 of the multi-channel endoprosthesis 80 is greater than the outer diameter of the second endoprosthesis 172. The first endoprosthesis 171 and the second endoprosthesis 172 are preferably sewn to the multi-channel endoprosthesis 80. The Y-shaped endoprosthesis 160 is preferably placed at the iliac cross-over.

The Y-shaped endoprosthesis 160 has a shape such that the entire flow of blood that arrives from the heart is divided between the two endoprostheses 171, 172.

Although FIG. 17 shows an embodiment of the invention wherein two endoprostheses 171, 172 are inserted into the third portion 83 and the second portion 82 of the multi-channel endoprosthesis 80, embodiments of the invention wherein
- a single endoprosthesis is inserted,
- more than two endoprostheses are inserted,
- the insertion is carried out solely in the third portion, or solely in the second portion in particular if the third portion is not present, are possible without leaving the scope of this invention.

The invention claimed is:

1. A flow-regulating luminal endoprosthesis (30) comprising at least one first section and one second section, with each one of the sections comprising a braided meshing, wherein at an end (35) of the endoprosthesis, one of the sections is turned over with respect to the other section in such a way as to for the endoprosthesis (30) comprising two coaxial sections (31, 32) separated by 0.5 mm to 4 mm and a turnover part (33) that joins the two sections (31, 32) and located at the end (35) of the endoprosthesis (30), wherein the coaxial sections (31, 32) comprise a material of which the elastic modulus is between 0.050 N/m$^2$ and 1 N/m$^2$.

2. The endoprosthesis as claimed in claim 1, wherein the meshing of the first and the second sections has a surface with a porosity of 60 to 75%.

3. The endoprosthesis as claimed in claim 1, wherein the meshing of the first and the second sections is such that a superposition of the first and second sections is permeable to blood.

4. The endoprosthesis as claimed in claim 1, wherein meshes forming the meshing of the first and the second sections have sides between 1 mm and 2 mm.

* * * * *